(12) United States Patent  
Gleich et al.

(10) Patent No.: US 8,264,220 B2
(45) Date of Patent: Sep. 11, 2012

(54) ARRANGEMENT AND METHOD FOR INFLUENCING AND/OR DETECTING MAGNETIC PARTICLES IN A REGION OF ACTION USING COIL ARRANGEMENT HAVING A SURROUNDING COIL THAT ALMOST COMPLETELY SURROUNDS A MAGNETIC FIELD GENERATOR

(75) Inventors: Bernhard Gleich, Hamburg (DE); Juergen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 451 days.

(21) Appl. No.: 12/519,420

(22) PCT Filed: Dec. 17, 2007

(86) PCT No.: PCT/IB2007/055165
§ 371 (c)(1),
(2), (4) Date: Jun. 16, 2009

(87) PCT Pub. No.: WO2008/078269
PCT Pub. Date: Jul. 3, 2008

(65) Prior Publication Data
US 2010/0045280 A1 Feb. 25, 2010

(30) Foreign Application Priority Data
Dec. 20, 2006 (EP) .................................. 06126578

(51) Int. Cl.
G01N 27/72 (2006.01)
G01R 33/12 (2006.01)
(52) U.S. Cl. .................... 324/228; 324/204; 324/240
(58) Field of Classification Search .................. None
See application file for complete search history.

(56) References Cited

U.S. PATENT DOCUMENTS

| | | | |
|---|---|---|---|
| 4,899,109 A | 2/1990 | Tropp et al. | |
| 5,309,106 A | 5/1994 | Miyajima et al. | |
| 5,572,131 A | 11/1996 | Rzedzian | |
| 2003/0085703 A1* | 5/2003 | Gleich | 324/309 |

FOREIGN PATENT DOCUMENTS

DE 10151778 A1 5/2003
(Continued)

OTHER PUBLICATIONS

Sullivan, C.: "Optimal Choice for Number of Strands in a Litz-Wire Transformer Winding", IEEE Transactions on Power Electronics, Vol. 14, No. 2, Mar. 1999, pp. 283-291.

(Continued)

*Primary Examiner* — Jay Patidar (57) ABSTRACT

An arrangement and a method for influencing and/or detecting magnetic particles in a region of action includes a selector for generating a magnetic selection field having a pattern in space of its magnetic field strength such that a first sub-zone having a low magnetic field strength and a second sub-zone having a higher magnetic field strength are formed in the region of action. A driver is provided for changing the position in space of the two sub-zones in the region of action by a magnetic drive field so that the magnetization of the magnetic particles changes locally. A receiver is also provided for acquiring signals, which signals depend on the magnetization in the region of action, which magnetization is influenced by the change in the position in space of the first and second sub-zone. Further, a coil arrangement is provided including a surrounding coil and a magnetic field generator such that the surrounding coil almost completely surrounds the magnetic field generator.

20 Claims, 5 Drawing Sheets

FOREIGN PATENT DOCUMENTS

| | | |
|---|---|---|
| EP | 1115005 A2 | 7/2001 |
| EP | 1145738 A2 | 10/2001 |
| EP | 1304542 A2 | 4/2003 |
| WO | 2004018039 A1 | 3/2004 |

OTHER PUBLICATIONS

Gleich. B. et al.: "Magnetic Particle Imaging (MPI)," Medicamundi, vol. 50, May 2006, pp. 66-71.

* cited by examiner

ARRANGEMENT AND METHOD FOR INFLUENCING AND/OR DETECTING MAGNETIC PARTICLES IN A REGION OF ACTION USING COIL ARRANGEMENT HAVING A SURROUNDING COIL THAT ALMOST COMPLETELY SURROUNDS A MAGNETIC FIELD GENERATOR

CROSS REFERENCE TO RELATED APPLICATIONS

This application claims the benefit of EP provisional application Ser. No. 06126578.1, filed Dec. 20, 2006, which is incorporated herein by reference. Related applications are PCT Ser. No. IB2007/055126, "Arrangement and Method for Influencing and/or Detecting Magnetic Particles in a Region of Action," filed Dec. 14, 2007, PCT Ser. No. IB2007/055152, "Arrangement for Influencing and/or Detecting Magnetic Particles in a Region of Action and Method of Producing a Disk Shaped Coil," filed Dec. 17, 2007, PCT Ser. No. IB2007/055157, "Arrangement and Method for Influencing and/or Detecting Magnetic Particles in a Region of Action," filed Dec. 17, 2007, PCT Ser. No. IB2007/055134, "Arrangement and Method for Influencing and/or Detecting Magnetic Particles in a Region of Action," filed Dec. 14, 2007, PCT Ser. No. IB2007/055174, "Arrangement and Method for Influencing and/or Detecting Magnetic Particles in a Region of Action," filed Dec. 17, 2007, PCT Ser. No. IB2007/055131, "Arrangement and Method for Influencing and/or Detecting Magnetic Particles in a Region of Action," filed Dec. 14, 2007, PCT Ser. No. IB2007/055158, "Arrangement and Method for Influencing and/or Detecting and/or Locating Magnetic Particles in a Region of Action," filed Dec. 17, 2007, PCT Ser. No. IB2007/055162, "Method and Arrangement for Locating Magnetic Markers in a Region of Action," filed Dec. 17, 2007, PCT Ser. No. IB2007/055178, "Arrangement and Method for Detecting and/or Locating a Magnetic Material in a Region of Action, Use of a Arrangement In the Examination of Buildings," filed Dec. 17, 2007, PCT Ser. No. IB2007/055177, "Method and Arrangement for Influencing and/or Detecting Magnetic Particles in a Region of Action," filed Dec. 17, 2007, PCT Ser. No. IB2007/055204, "Method and Arrangement for Separating Magnetic Particles, Magnetic Particles and Use of Magnetic Particles," filed Dec. 18, 2007, and PCT Ser. No. IB2007/055163, "Influencing and/or Detecting Magnetic Particles in a Region of Action of a Examination Object," filed Dec. 17, 2007.

The present invention relates to an arrangement for influencing and/or detecting magnetic particles in a region of action and to a coil arrangement. Furthermore, the invention relates to a method for influencing and/or detecting magnetic particles in a region of action.

The arrangement and the method of this kind is known from German patent application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e.g. human bodies—in a non-destructive manner and without causing any damage and with a high spatial resolution, both close to the surface and remote from the surface of the examination object.

An object of the present invention is to provide an arrangement which is less bulky and where a magnetic field generator, e.g. a permanent magnet, can be used very efficiently. A further object is to improve the quality of the magnetic field generating means and/or of the magnetic drive field generating means and to reduce the power consumption.

The above object is achieved by an arrangement for influencing and/or detecting magnetic particles in a region of action, wherein the arrangement comprises selection means for generating a magnetic selection field having a pattern in space of its magnetic field strength such that a first sub-zone having a low magnetic field strength and a second sub-zone having a higher magnetic field strength are formed in the region of action, drive means for changing the position in space of the two sub-zones in the region of action by means of a magnetic drive field so that the magnetization of the magnetic particles changes locally, receiving means for acquiring signals, which signals depend on the magnetization in the region of action, which magnetization is influenced by the change in the position in space of the first and second sub-zone, wherein the arrangement comprises a coil arrangement comprising a surrounding coil and a magnetic field generator such that the surrounding coil almost completely surrounds the magnetic field generator.

Such an arrangement has the advantage that the interior of the coil arrangement can be used for the magnetic field generator, thereby reducing the necessary space for the magnetic field generator. Furthermore, the mutual disturbances of the surrounding coil on the one hand and of the magnetic field generator on the other hand can be largely reduced by the arrangement of the present invention. Especially, no eddy currents are induced in the interior of the surrounding coil, which eddy currents could disturb the magnetic field generator. The magnetic field generator is preferably provided as a permanent magnet but it can also be provided as, e.g. a superconducting structure. In the following, the term magnetic field generator and permanent magnet are used synonymously.

According to the present invention, it is preferred that the coil arrangement is provided in a ring shape or in a square ring shape. A ring shape in the context of the present invention shall have the meaning of a torus shape. A torus shape is meant to be a doughnut-shaped surface generated by a circle rotated about an axis always being perpendicular to the plane of the circle and not intersecting the circle. A square ring shape in the context of the present invention shall have the meaning of a quasi torus shape, i.e. for example a surface generated by a square or a rectangle rotated about an axis always being perpendicular to the plane of the square or the rectangle and not intersecting the square or the rectangle. Furthermore a quasi torus shape corresponds also to the form shown in FIG. 13 having a center line that can be approximated by a square and which has at least in most parts along the center line a cross section which is also approximated by a square. Thereby, it is possible according to the present invention to almost completely surround the permanent magnet by the surrounding coil. This has the advantage that no or only minimal disturbances of the magnetic field enter the interior of the surrounding coil such that the material of the permanent magnet does at least not experience a time-varying magnetic field. According to the present invention, further shapes of the surrounding coil are possible, e.g. the generating circle or the generating square (i.e. the shape of a cross section of the surrounding coil) can be formed differently, e.g. it can be provided elliptically, polygonal, triangular, pentagonal, hexagonal, heptagonal, octagonal or the like or comprising a distortion in one or a plurality of directions. Furthermore and for each one of these variations of the generating shape, the center line can be shaped differently than circular or square, e.g. elliptically, polygonal, triangular, pentagonal, hexagonal, heptagonal, octagonal or the like or comprising a distortion in one or a plurality of directions.

Very preferably according an embodiment of the present invention, the surrounding coil of the coil arrangement comprises at least one discrete capacitor and/or at least one distributed capacitor. Thereby, the coil arrangement can be provided resonant such that an oscillation can be generated with very low power consumption.

Furthermore according to a preferred embodiment of the present invention, it is preferred according to the present invention, that the coil arrangement comprises a cooling channel between the surrounding coil and the permanent magnet. Thereby, it is advantageously possible to efficiently cool the coil arrangement and to easily define its temperature. The cooling can be done using conventional cooling fluids, e.g. water (especially as there are no high voltages) or oil.

According to a preferred embodiment of the present invention the surrounding coil of the arrangement comprises at least one layer of a conductor foil and according to another preferred embodiment of the present invention, the surrounding coil of the coil arrangement comprises at least one printed circuit board material comprising at least one layer of conductive material. Thereby, it is possible according to these embodiments to precisely define the current supporting areas and surfaces of the surrounding coil.

Very preferably according to one embodiment, the conductor foil or the conductive material having a thickness of 1 µm to 50 µm and furthermore preferably the thickness of the conductor foil or of the conductive material increases from outer layers towards inner layers. Thereby, it is e.g. possible to control the current in the current supporting surfaces in a very efficient manner at different frequencies applied to the surrounding coil. In one preferred embodiment, the increase in thickness of the conductive material from outer layers towards inner layers is realized such that at least one innermost layer is provided having a greater thickness than the other layers. The residual layers (except the innermost layers) can have but do not need to have different thickness in that embodiment. Furthermore, it is preferred that the thickness and the capacitors of the layers of the conductor foil and/or of the layers of the conductive material are provided such that each layer of the conductive foil and each layer of the conductive material supports approximately the same current density. In the context of the present invention, by the term "approximately the same current density" in different layers is meant that the current density differs less than e.g. a factor of 2 or 3, preferably a factor of 1.5. By distributing the current supporting material in different layers or generally by splitting the current supporting material, it is possible according to the present invention to provide an increased current supporting area compared to the situation that the current distribution is provided "naturally" in one single layer or in one single (non splitted) material (mainly in the skin depth). Thereby, an optimal distribution of the current is possible such that the overall resistance of the surrounding coil is minimal leading to a reduced power consumption and to a reduce heat development in the region of the coil arrangement. Furthermore, this avoids unnecessary heat transfer to the permanent magnet, thereby increasing the stability of the magnetic field generated by the permanent magnet. According to an embodiment of the present invention, it is possible to provide the innermost conductor foil having a greater thickness.

Very preferably according to another embodiment of the present invention, the surrounding coil of the arrangement comprises at least partially a litz wire and/or the litz wire comprises a plurality of individual wires, each individual wire being surrounded by an electrically high resistive material. The litz wire is preferably oriented around the ring shape of the coil arrangement, i.e. parallel to the centerline. This enables a very efficient realization of the current supporting paths of the coil arrangement. Furthermore, it is thereby possible to provide a very high current supporting surface inside the litz wire which is important both for the case that an AC current with a comparably high frequency is to be supported by the litz wire and for the case that a DC current or an AC current having a comparably low frequency is to be supported by the litz wire but in the presence of a static and/or an dynamic magnetic field that penetrates the litz wire. According to the present invention, it is preferred that the litz wire is spun such that one individual wire is e.g. in the center of the litz wire at one position along the extension direction of the litz wire and that this individual wire is e.g. in the periphery of the litz wire at another position along the extension direction of the litz wire. Thereby it is possible that each one of all the individual wires is preferably provided such that, e.g. in a loop formed by the litz wire, the same impedance is realized by each individual wire.

According to a further preferred embodiment of the present invention, the individual wires of the litz wire have a diameter of approximately 1 µm to approximately 50 µm, preferably of approximately 10 µm to approximately 25 µm. Thereby, an optimal distribution of the current is possible such that the overall resistance of the surrounding coil is minimal. It is furthermore preferred according to an embodiment of the present invention that the litz wire comprises a plurality of first order litz wires comprising a plurality of individual wires, wherein the litz wire comprises a plurality of first order litz wires. In a preferred embodiment of the present invention, the litz wire comprises a plurality of first order litz wires and a plurality of second order litz wires, wherein the first order litz wires comprise a plurality of individual wires, wherein the second order litz wires comprise a plurality of first order litz wires, and wherein the litz wire comprises a plurality of second order litz wires. Thereby, an increase in current supporting surface is possible and the complexity of the handling requirements—especially the possibility of bending the litz wire comprising a multitude of individual wires—are reduced.

The invention further relates to a coil arrangement comprising a surrounding coil and a permanent magnet, the coil arrangement being provided such that the surrounding coil almost completely surrounds the permanent magnet.

Such a coil arrangement has the advantage that the interior of the surrounding coil is completely free of at least a changing magnetic field. This allows the permanent magnet to produce a very stable magnetic field. All the preferred measures according to embodiments of the inventive arrangement also apply to the inventive coil arrangement.

The present invention further refers to the use of an inventive arrangement for influencing and/or detecting magnetic particles in a region of action, furthermore to the use of an inventive coil arrangement and still furthermore to a method for influencing and/or detecting magnetic particles in a region of action, wherein the method comprises the steps of generating a magnetic selection field having a pattern in space of its magnetic field strength such that a first sub-zone having a low magnetic field strength and a second sub-zone having a higher magnetic field strength are formed in the region of action, changing the position in space of the two sub-zones in the region of action by means of a magnetic drive field so that the magnetization of the magnetic particles changes locally, acquiring signals, which signals depend on the magnetization in the region of action, which magnetization is influenced by the change in the position in space of the first and second sub-zone, wherein the generation of the magnetic selection field and/or the change of the position in space of the two sub-zones is performed at least partially by means of a coil arrangement comprising a surrounding coil and a permanent magnet such that the surrounding coil almost completely surrounds the permanent magnet.

Thereby, the beneficial effects of a reduced disturbance of the permanent magnet inside the coil arrangement can be realized very efficiently.

The selection means comprise magnetic field generation means that provide either a static (gradient) magnetic selection field and/or a comparably slowly changing long range magnetic selection field with frequencies in the range of about 1 Hz to about 100 Hz. Both the static part and the comparably slowly changing part of the magnetic selection field can be generated by means of the permanent magnet inside the coil arrangement or by means of coils or by a combination thereof. The drive means comprise magnetic field generation means that provide a magnetic drive field with frequencies in the range of about 1 kHz to about 200 kHz, preferably about 10 kHz to about 100 kHz.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
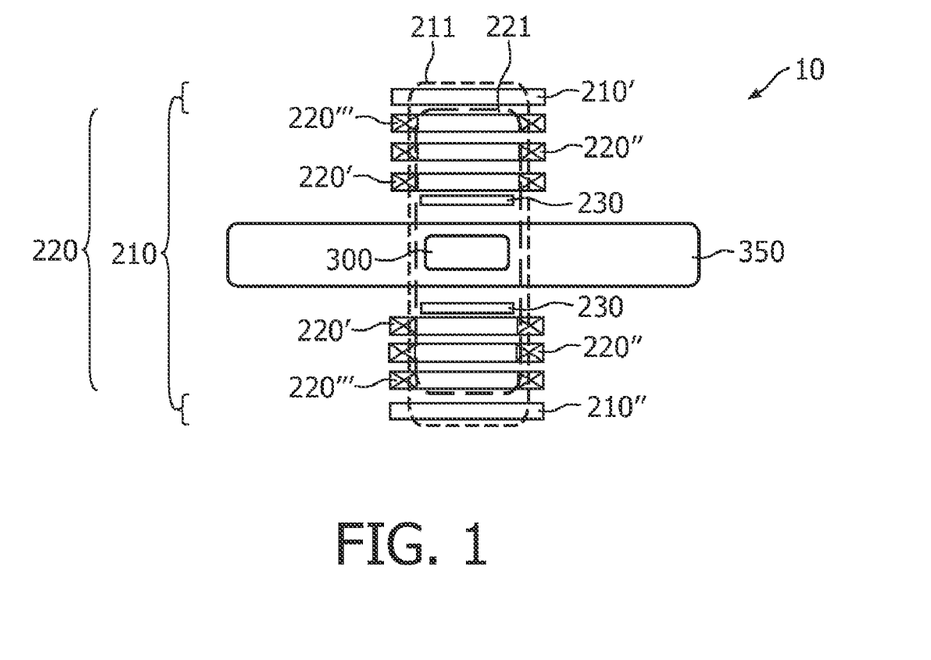
FIG. 1 illustrates an arrangement according to the present invention for carrying out the method according to the present invention.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
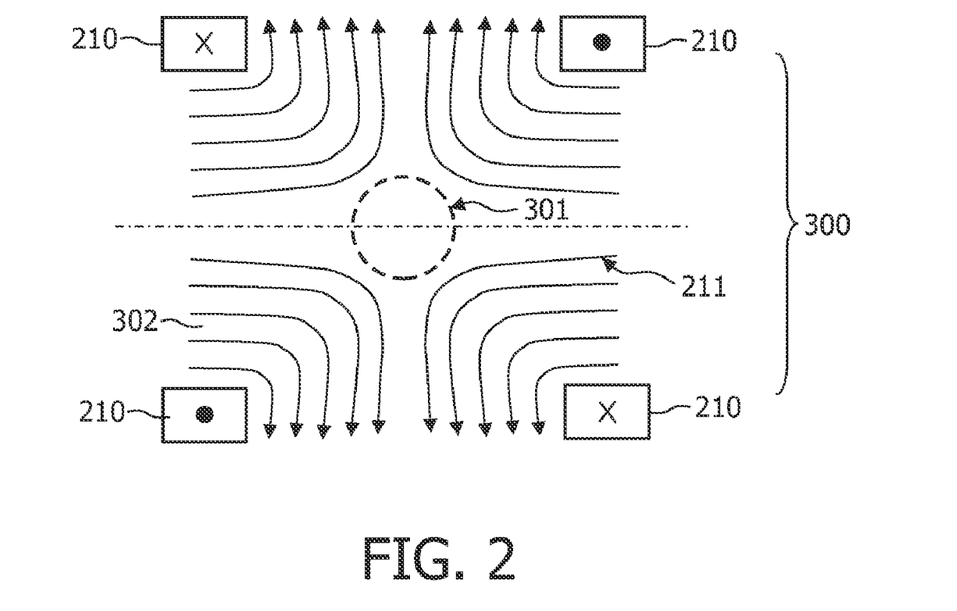
FIG. 2 illustrates an example of the field line pattern produced by an arrangement according to the present invention

As an example of an embodiment of the present invention, an arrangement 10 is shown in FIG. 2 comprising a plurality of coils forming a selection means 210 whose range defines the region of action 300 which is also called the region of examination 300. For example, the selection means 210 is arranged above and below the object 350. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of the magnetic particles 100 present in that first sub-zone 301 is not saturated, whereas the magnetization of the magnetic particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the magnetic particles 100 in a state of saturation. By changing the position of the two sub-zones 301, 302 within the region of action 300, the (overall) magnetization in the region of action 300 changes. By measuring the magnetization in the region of action 300 or a physical parameter influenced by the magnetization, information about the spatial distribution of the magnetic particles 100 in the region of action can be obtained.

When a further magnetic field—in the following called a magnetic drive field 221 is superposed on the magnetic selection field 211 (or gradient magnetic field 211) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics, i.e. the due to saturation effects.

In order to generate the magnetic drive field 221 for any given direction in space, there are provided three drive coil pairs, namely a first drive coil pair 220', a second drive coil pair 220" and a third drive coil pair 220'" which together are called drive means 220 in the following. For example, the first drive coil pair 220' generates a component of the magnetic drive field 221 which extends in a given direction, i.e. for example vertically. To this end the windings of the first drive coil pair 220' are traversed by equal currents in the same direction. The two drive coil pairs 220", 220'" are provided in order to generate components of the magnetic drive field 221 which extend in a different direction in space, e.g. horizontally in the longitudinal direction of the region of action 300 (or the patient 350) and in a direction perpendicular thereto. If second and third drive coil pairs 220", 220'" of the Helmholtz type were used for this purpose, these drive coil pairs would have to be arranged to the left and the right of the region of treatment or in front of and behind this region, respectively. This would affect the accessibility of the region of action 300 or the region of treatment 300. Therefore, the second and/or third magnetic drive coil pairs or coils 220", 220'" are also arranged above and below the region of action 300 and, therefore, their winding configuration must be different from that of the first drive coil pair 220'. Coils of this kind, however, are known from the field of magnetic resonance apparatus with open magnets (open MRI) in which a radio frequency (RF) drive coil pair is situated above and below the region of treatment, said RF drive coil pair being capable of generating a horizontal, temporally variable magnetic field. Therefore, the construction of such coils need not be further elaborated herein.

According to the present invention, the selection means 210 and/or the drive means 220 can be provided comprising at least one permanent magnet inside a surrounding coil. Such an arrangement of a permanent magnet and a surrounding coil is also called a coil arrangement. For example the permanent magnet of such a coil arrangement can be part of the selection means and the surrounding coil can be part of the drive means. Especially, two coil arrangements are provided in an inventive arrangement for influencing and/or detecting magnetic particles, e.g. in a concentric configuration. Examples of such coil arrangements are described below and shown in FIGS. 8 to 15.

The arrangement 10 according to the present invention further comprise receiving means 230 that are only schematically shown in FIG. 1. The receiving means 230 usually comprise coils that are able to detect the signals induced by the magnetization pattern of the magnetic particle 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein. According to the present invention, it is preferred that the resistance of the receiving means is dominated by thermal noise, especially generated by thermal noise due to the presence of the magnetic particles in the region of action, i.e. the resistance of the current supporting paths without the presence of the magnetic particles in the region of action is comparable or smaller than the resistance in presence of the magnetic particles in the region of action. This is achieved in particular by means of carefully defining the individual current paths, current strength, wire configuration and other characteristics of the receiving means.

Such an arrangement and such a method of detecting magnetic particles are known from DE 101 51 778 which is hereby incorporated in its entirety.

Figure 3:
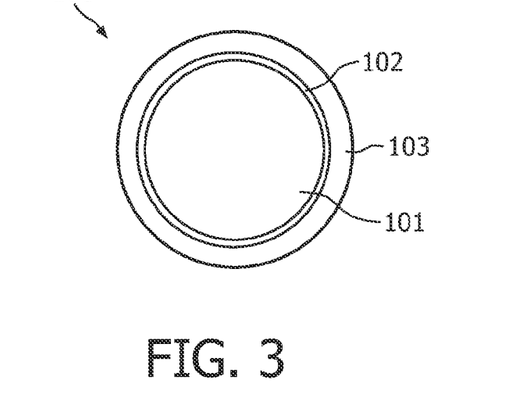
FIG. 3 illustrates an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to $160 \cdot 10^3$ A/m2, the first sub-zone 301 in which the magnetization of the particles 100 is not saturated has dimensions of about 1 mm (in the given space direction). By increasing the magnetic field strength and especially the magnetic gradient strength of the magnetic selection field 211, it is possible to enhance the spatial resolution of the arrangement 10 according to the present invention.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
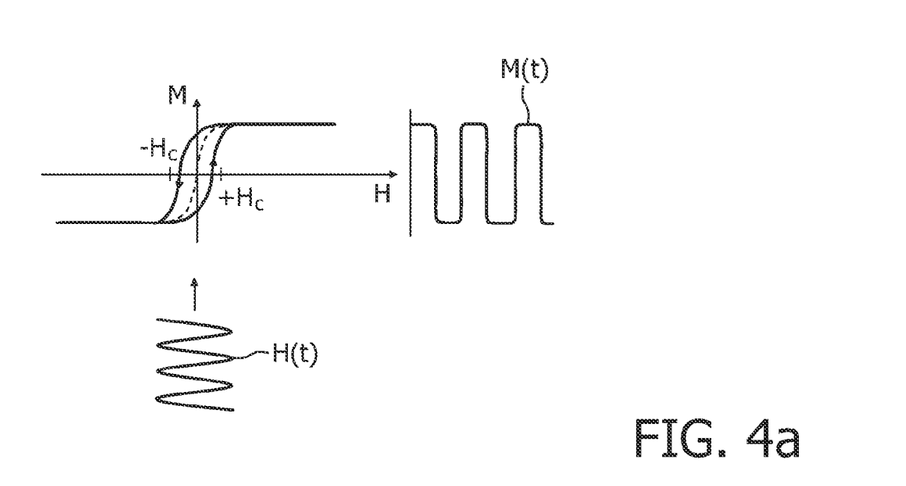
FIGS. 4a and 4b illustrate the magnetization characteristics of such particles.
Figure 4B:
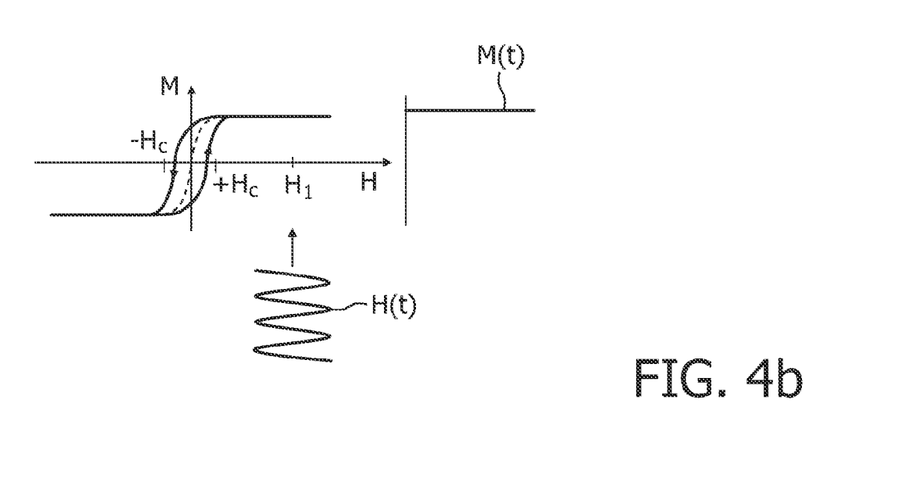

FIGS. 4*a* and 4*b* show the magnetization characteristic, that is, the variation of the magnetization M of a particle 100 (not shown in FIGS. 4*a* and 4*b*) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4*a* illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4*a*. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4*b* shows the effect of a sinusoidal magnetic field H(t) on which a static magnetic field Hi is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
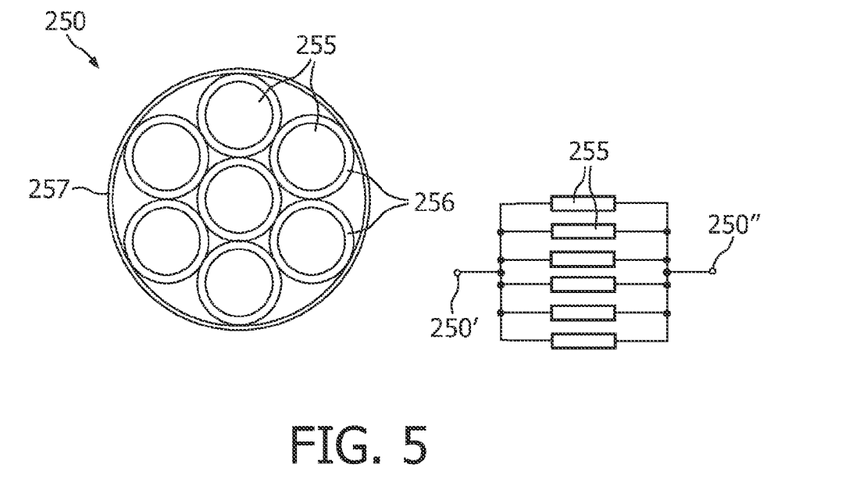
FIGS. 5 to 7 illustrate schematically different examples of litz wire configurations.
Figure 6:
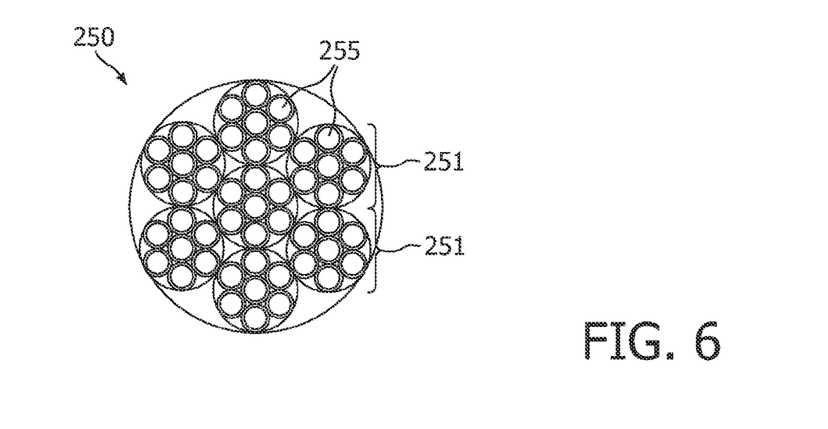
Figure 7:
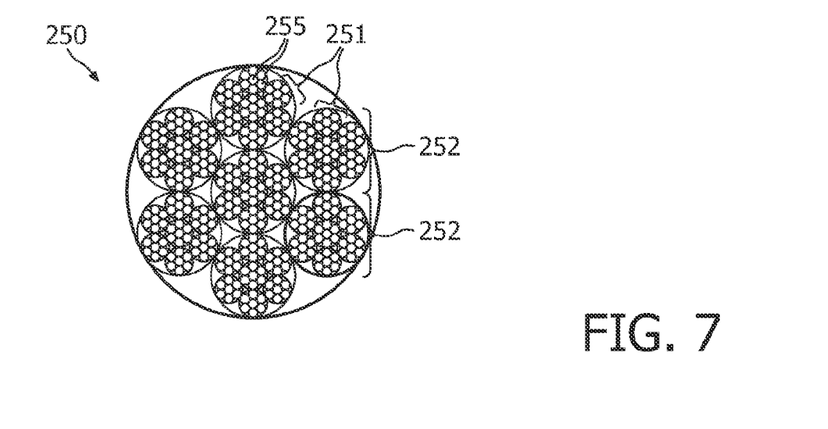

In one embodiment of the present invention, it is proposed to provide the coil arrangement at least partially with a litz wire 250 which is explained in greater details in FIGS. 5 to 7. In FIGS. 5 to 7 the litz wire 250 is shown in a schematical representation. Each of these figures represents a cross sectional view of one embodiment of such a litz wire 250 according to the present invention. Each litz wire 250 comprises a multitude of individual wires 255. The representations of the various embodiments are not drawn to scale and the dimensions are chosen for the sake of representation simplicity only. The filling factor of the litz wire 250 can easily be evaluated by means of summing up the cross sectional areas of each of the individual wires 255 and dividing by the cross sectional area of the complete litz wire 250. By means of applying a pressure to the embodiments of the litz wire 250 represented in FIGS. 5 to 7 in a direction perpendicularly to the longitudinal extension of the litz wire 250, the filling factor can be enhanced. Each individual wire 255 is preferably surrounded circumferentially by an electrically high resistive material 256 which acts in the manner of a cladding 256 for each individual wire 255. It is to be understood that it is preferred according to the present invention that such a cladding material 256 is present at each individual wire 255; however such a continuous cladding 256 is not necessary if the condition is fulfilled that each individual wire 255 of the litz wire 250 is electrically isolated from the adjacent individual wires 250 between a first end 250' of the litz wire and a second end 250" of the litz wire 250. The individual wires 255 of the litz wire 250 act as individual current supporting paths 255 and can be regarded as resistors connected in parallel and having ideally an identical impedance as shown by the equivalent circuit diagram represented on the right hand side in FIG. 5. Therefore it is preferred according to the present invention, that the litz wire is spun such that one individual wire is e.g. in the center of the litz wire at one position along the extension direction of the litz wire and that this individual wire is e.g. in the periphery of the litz wire at another position along the extension direction of the litz wire. In the embodiment of the litz wire 250 represented in FIG. 5, a further preferred feature of the litz wire 250 is represented, namely a plastic foil insulation 257 is provided collectively around the individual wires 255. Such a plastic (e.g. thermoplastic) insulation can also be provided to all the other embodiments of the litz wire 250 but is not shown there. The additional feature of such an insulation foil or insulation material 257 collectively around the individual wires 255 of the litz wire 250 provides the advantage that a better high voltage performance of the litz wire is possible.

In FIG. 6 a cross sectional view of a further embodiment of the litz wire 250 is schematically shown where the litz wire 250 comprises also a plurality of individual wires 255 (as in the embodiment according to FIG. 5) but with the individual wires 255 grouped in a plurality of so-called first order litz wires 251. These first order litz wires 251 (each comprising a plurality of individual wires 255) are combined together to form the litz wire 250. In FIG. 6, the continuous cladding 256 is preferably present around each individual wire 255 but not indicated by means of a reference numeral.

In FIG. 7 a cross sectional view of a still further embodiment of the litz wire 250 is schematically shown where the litz wire 250 comprises also a plurality of individual wires 255 (as in the embodiments according to FIGS. 5 and 6) and a plurality of first order litz wires 251 but with the first order litz wires 251 grouped in a plurality of so-called second order litz wires 252. These second order litz wires 252 (each comprising a plurality of first order litz wires 251) are combined together to form the litz wire 250. In FIG. 6, the continuous cladding 256 is preferably present around each individual wire 255 but not represented for the sake of simplicity.

Figure 8:
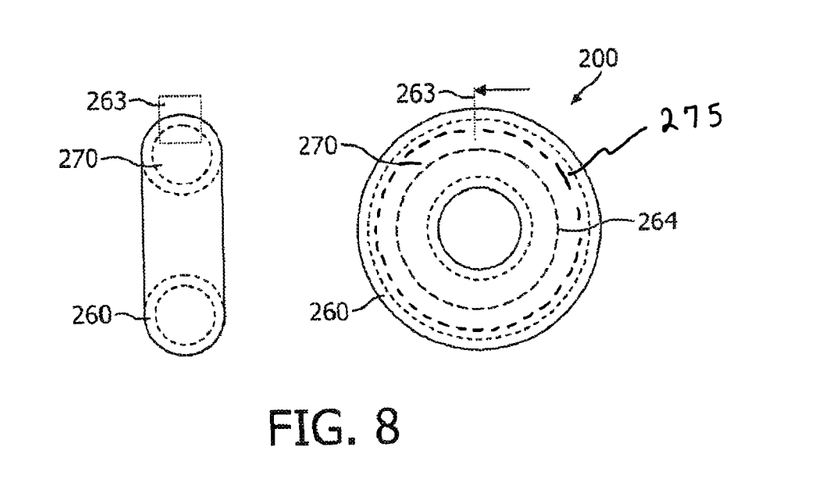
FIGS. 8 to 15 illustrate schematically different examples of the coil arrangement or parts thereof.

In FIGS. 8 to 15 different embodiments of coil arrangements 200 are shown. FIG. 8 schematically shows the overall representation of such a coil arrangement 200. On the left hand side of FIG. 8, a side view of the coil arrangement 200 is shown. On the right hand side of FIG. 8, a top view of the coil arrangement 200 is shown. The coil arrangement 200 comprises a permanent magnet 270 which is almost completely surrounded by a surrounding coil 260. The permanent magnet 270 is represented in FIG. 8 with small-dashed circular lines. The shape of the coil arrangement 200 is preferably a ring shape, also called a torus shape. This shape can be thought as being generated by a generating circle (not represented) which is rotated around a centreline of the torus. The centreline of the torus is represented on the right hand side of FIG. 8 with a long-dashed circular line and the reference sign 264. The generating circle is moved along the centreline 264, the tangent (not represented) of the centreline 264 always being perpendicular to the generating circle and going through the centre of the generating circle. As can be seen from FIG. 8, the permanent magnet 270 and the surrounding coil 260 can be spaced apart by a cooling channel 275. Furthermore, FIG. 8 depicts at reference sign 263 a section line (right hand side of FIG. 8) and a rectangular section (left hand side of FIG. 8) which is represented in an enlarged representation in FIGS. 11 and 12.

Figure 9:
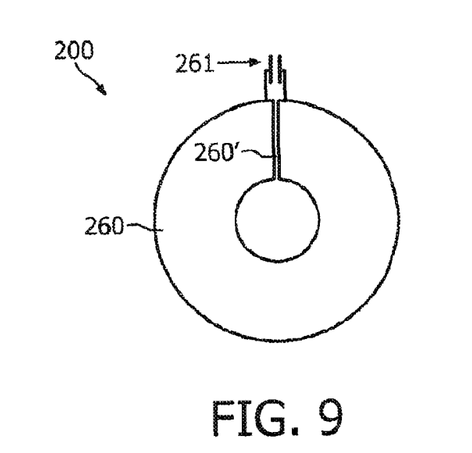
Figure 10:
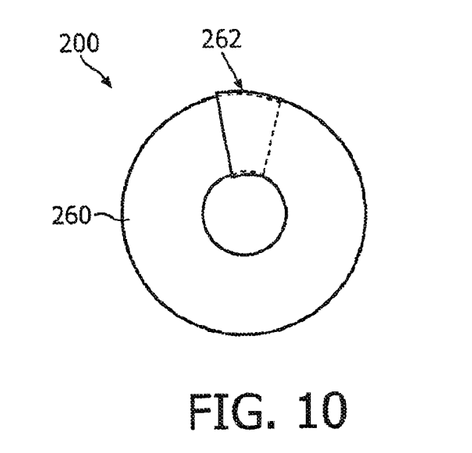

In FIGS. 9 and 10, two different preferred embodiments of the coil arrangement 200 are schematically shown. In the embodiment of FIG. 9, the surrounding coil 260 of the coil arrangement 200 comprises a discrete capacitor 261. In the embodiment of FIG. 10, the surrounding coil 260 of the coil arrangement 200 comprises a distributed capacitor 262. It is to be understood that both in FIG. 9 and in FIG. 10, the permanent magnet is meant to be placed inside the surrounding coil 260. The capacitors 261, 262 are preferred according to these embodiments of the present invention in order to provide a resonant coil arrangement 200. Thereby, it is possible to provide comparably strong magnetic fields—e.g. as forming components of the magnetic selection field 211 and/ or of the magnetic drive field 221—by means of the surrounding coil 260 with a relatively low power consumption.

The discrete capacitor 261 (FIG. 9) is preferably mounted to the outside of the surrounding coil 260, its two terminals being electrically coupled to the two ends of the surrounding coil facing each other across a gap 260' applied to the surrounding coil in order to electrically isolate the ends of the surrounding coil. The gap 260' and the discrete capacitor 261 joining the end of the gap 260' can also be provided twice (not represented) or even in higher number, especially uniformly distributed around the periphery of the surrounding coil 260.

The distributed capacitor 262 (FIG. 10) is preferably realized by means of overlapping parts of the surrounding coil 260, the overlapping parts being electrically isolated from each other to form a capacity. For example, if the surrounding coil 260 is realized by means of a circularly bent pipe, then the distributed capacitor 262 can be realized by telescoping the ends of the pipe into one another (thereby adapting their diameter at the location of the distributed capacitor 262). This is schematically shown in FIG. 10.

Figure 11:
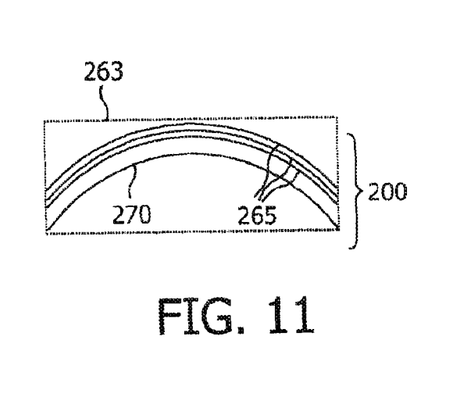
Figure 12:
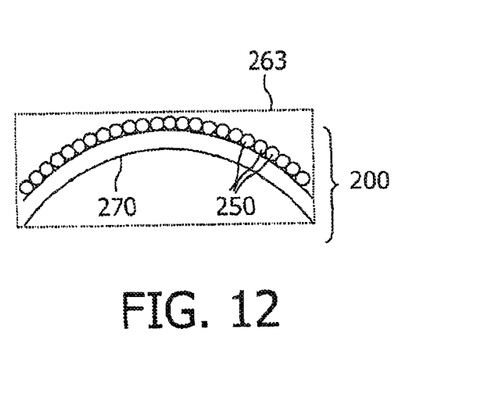

In FIGS. 11 and 12, two representations of the section 263 (shown in FIG. 8) and seen along an arrow (shown in FIG. 8) are schematically represented for the cases of two preferred embodiments of the present invention in order to illustrate the structure of the surrounding coil 260 according to these embodiments. In the embodiment according to FIG. 11, a plurality of layers of a conductor foil 265 are formed along the entire ring shaped surface of the surrounding coil 260, each of the layers of the conductor foil 265 preferably being provided such that it forms overlapping areas where the ends of that layer of the conductor foil 265 are overlapping in order to produce a distributed capacitor 262 similar to the representation of FIG. 10. The layers of the conductor foil 265 are isolated from each other by means of an insulation material (not represented in FIG. 11) of small electrical conductivity.

Towards the centreline (not shown) of the coil arrangement 200, the permanent magnet 270 is schematically shown. In the embodiment according to FIG. 12, a plurality of litz wires 250 are formed along the entire ring shaped surface of the surrounding coil 260 and parallel to the centreline (not shown) of the coil arrangement 200. The ends of these litz wires 250 are preferably connected in parallel to one or a plurality of discrete capacitors 261 as schematically shown in FIG. 9. Towards the centreline (not shown) of the coil arrangement 200, the permanent magnet 270 is schematically shown.

Figure 13:
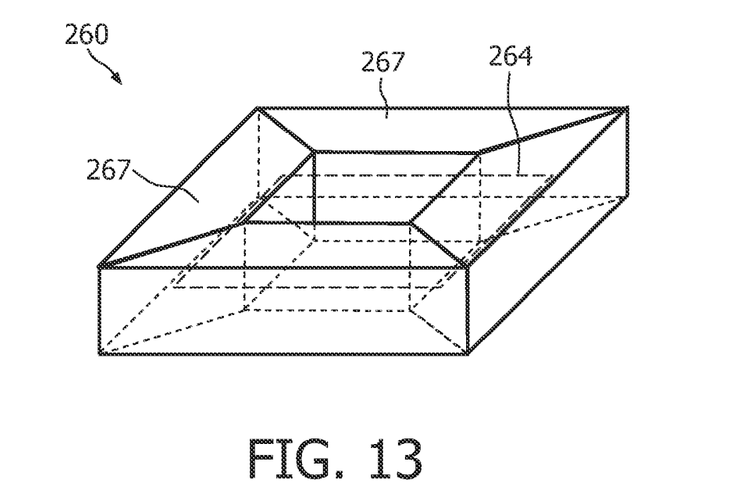
Figure 14:
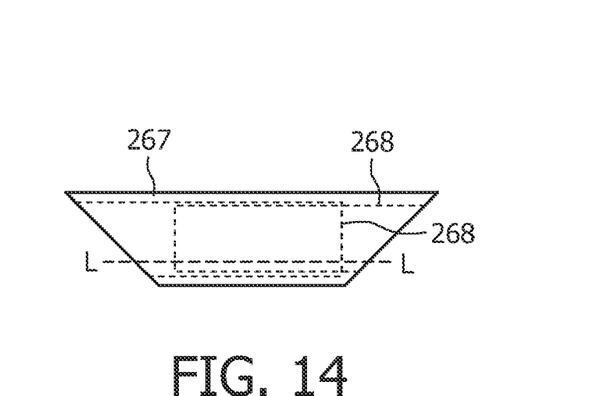
Figure 15:
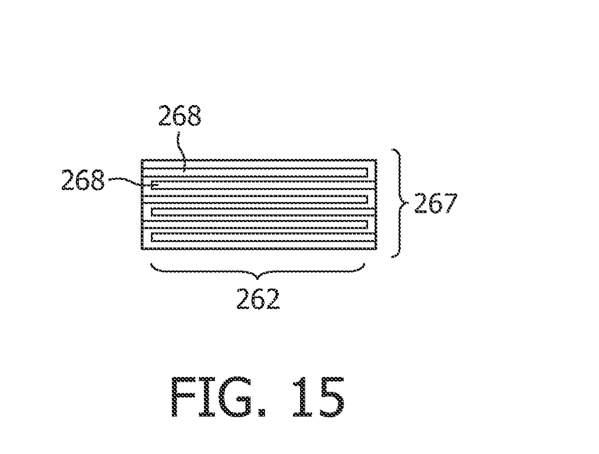

In FIGS. 13 to 15, a further embodiment of the coil arrangement 200 is schematically shown. In this embodiment of the coil arrangement 200, the coil arrangement 200 can have a quasi ring shape as represented in the perspective representation of FIG. 13. The shape of such a coil arrangement 200 can be thought as being generated by means of a square or a rectangle which is moved along a square centreline 264 represented with a long-dashed line in FIG. 13. The quasi ring shaped form of the coil arrangement 200 can be realized by means of flat rectangular formed elements and by means of flat trapeze formed elements, the trapeze formed elements constituting the top and bottom surface of the quasi ring shaped surrounding coil 260 and the rectangular formed elements constituting the vertical surfaces (inner square and outer square) of the quasi ring shaped surrounding coil 260. The trapeze and rectangular formed elements are preferably provided in the form of printed circuit board material 267 comprising at least one layer of conductive material 268, preferably a plurality of layers of conductive material 268. An example of a trapeze shaped element in the form of the circuit board material 267 is shown in FIG. 14. In FIG. 14, it is furthermore schematically represented that the at least one layer of conductive material 268 inside the circuit board material 267 is preferably arranged in an overlapping configuration. This is further represented in FIG. 15, where a cross sectional view of the printed circuit board material 267 is shown along a section line L-L, represented in FIG. 14. In FIG. 15, three different layers of conductive material 268 are shown where the three layers each realize an overlapping area and thereby realizing a distributed capacitor 262 (similar to the embodiment shown in FIG. 11). The thickness of the representation of FIG. 15 is not drawn to scale and is exaggerated compared to the top view representation of the trapeze element of printed circuit board material 267 shown in FIG. 14. Between the layers of conductive material 268 is provided a material of low conductivity in order to isolate the layers. The surrounding coil 260 according to the embodiment shown in FIGS. 13 to 15 is assembled by joining the at least one layer of conductive material 268 at the joints of the trapeze and rectangular elements respectively. Thereby, the conductive material 268 is closed in each layer around the permanent magnet 270.

Both the layers of the conductive material 268 inside the printed circuit board material 267 (FIGS. 13 to 15) and the layers of the conductor foil 265 (FIG. 11) are preferably provided with a thickness of about 1 µm to about 50 µm, preferably with thickness such that the sum of the thickness of the plurality of layers is provided in the order of magnitude of the skin depth of the surrounding coil 260 at the highest usual frequency of operation. Preferably, the thickness of the layers of the conductor foil 265 and/or of the conductive material 268 are not provided equally in each of the plurality of layers but increases from outer layers to inner layers (not shown in the Figures). Thereby (and by adjusting the capacitances of the capacitors), it is possible to provide approximately the same current density in each of the different layers. Thereby, it is advantageously possible use the available current supporting material (conductive material 268, conductor foil 265) in the most efficient manner for supporting the current flowing in the surrounding coil 260.

The invention claimed is:

1. An arrangement for at least one of influencing and detecting magnetic particles in a region of action, wherein the arrangement comprises:
    a selector configured to generate a magnetic selection field having a pattern in space of its magnetic field strength such that a first sub-zone having a low magnetic field strength and a second sub-zone having a higher magnetic field strength are formed in the region of action;
    a driver configured to change a position in space of the first sub-zone and the second sub-zone in the region of action by a magnetic drive field so that magnetization of the magnetic particles changes locally;
    a receiver configured to acquire signals, wherein the signals depend on the magnetization in the region of action and wherein the magnetization is influenced by the change in the position in space of the first sub-zone and second sub-zone; and
    a coil arrangement comprising a surrounding coil which is part of the driver and at least partially generates the magnetic drive field, and a magnetic field generator which is part of the selector and at least partially generates the magnetic selection field such that the surrounding coil almost completely surrounds the magnetic field generator.

2. The arrangement according to claim 1, wherein the surrounding coil of the coil arrangement comprises at least one discrete capacitor.

3. The arrangement according to claim 1, wherein the coil arrangement comprises a cooling channel between the surrounding coil and the magnetic field generator.

4. The arrangement according to claim 1, wherein the surrounding coil of the coil arrangement comprises at least one distributed capacitor.

5. The arrangement according to claim 1, wherein the surrounding coil of the coil arrangement comprises at least one layer of a conductor foil.

6. The arrangement according to claim 5, wherein the conductor foil has a thickness of 1 μm to 50 μm.

7. The arrangement according to claim 5, wherein a thickness of the conductor foil increases from outer layers towards inner layers.

8. The arrangement according to claim 5, wherein at least one of a thickness and a capacitance of the at least one layer of the conductor foil is configured such that each layer of the conductive foil supports approximately a same current density.

9. The arrangement according to claim 1, wherein the surrounding coil of the coil arrangement comprises at least one printed circuit board material comprising at least one layer of conductive material.

10. The arrangement according to claim 9, wherein the conductive material has a thickness of 1 μm to 50 μm.

11. The arrangement according to claim 9, wherein a thickness of the conductive material increases from outer layers towards inner layers.

12. The arrangement according to claim 9, wherein at least one of a thickness and a capacitance of the layers of the conductive material is configured such that each layer of the conductive material supports approximately a same current density.

13. The arrangement according to claim 1, wherein the surrounding coil of the coil arrangement comprises at least partially a litz wire.

14. The arrangement according to claim 13, wherein the litz wire comprises a plurality of individual wires, each individual wire being surrounded by an electrically high resistive material.

15. The arrangement according to claim 13, wherein individual wires of the litz wire have a diameter of approximately 1 μm to approximately 50 μm.

16. The arrangement according to claim 10, wherein individual wires of the litz wire have a diameter of 10 μm to 25 μm.

17. The arrangement of claim 1, wherein the magnetic field generator comprises a permanent magnet.

18. A method for at least one of influencing and detecting magnetic particles in a region of action, wherein the method comprises the acts of:
    generating by a selector a magnetic selection field having a pattern in space of its magnetic field strength such that a first sub-zone having a low magnetic field strength and a second sub-zone having a higher magnetic field strength are formed in the region of action;
    changing by a driver a position in space of the first sub-zone and the second sub-zone in the region of action by a magnetic drive field so that magnetization of the magnetic particles changes locally;
    acquiring signals, wherein the signals depend on the magnetization in the region of action, wherein the magnetization is influenced by the change in the position in space of the first sub-zone and the second sub-zone;
    wherein at least one of the generating act and the changing act is performed at least partially by a coil arrangement comprising a surrounding coil which is part of the driver and at least partially generates the magnetic drive field, and a magnetic field generator which is part of the selector and at least partially generates the magnetic selection field such that the surrounding coil almost completely surrounds the magnetic field generator.

19. The method claim 18, wherein the magnetic field generator comprises a permanent magnet.

20. An arrangement for at least one of influencing and detecting magnetic particles in a region of action, wherein the arrangement comprises:
    a selector configured to generate a magnetic selection field having a pattern in space of its magnetic field strength such that a first sub-zone having a low magnetic field strength and a second sub-zone having a higher magnetic field strength are formed in the region of action;
    a driver configured to change a position in space of the first sub-zone and the second sub-zone in the region of action by a magnetic drive field so that magnetization of the magnetic particles changes locally;
    a receiver configured to acquire signals, wherein the signals depend on the magnetization in the region of action and wherein the magnetization is influenced by the change in the position in space of the first sub-zone and second sub-zone; and
    a coil arrangement comprising a surrounding coil which is part of the driver and at least partially generates the magnetic drive field, and a magnetic field generator which is part of the selector and at least partially generates the magnetic selection field such that the surrounding coil almost completely surrounds the magnetic field generator,
    wherein the surrounding coil of the coil arrangement comprises at least one capacitor.

* * * * *